United States Patent [19]
Mena

[11] Patent Number: 5,551,872
[45] Date of Patent: Sep. 3, 1996

[54] DENTAL IMPRESSION DEVICE

[76] Inventor: Raul Mena, 201 N. University Dr., Suite 101, Plantation, Fla. 33324

[21] Appl. No.: 315,519
[22] Filed: Sep. 30, 1994
[51] Int. Cl.⁶ .................................................. A61C 9/00
[52] U.S. Cl. ............................................................ 433/37
[58] Field of Search ................................. 433/37, 38, 41, 433/42, 43, 44, 45, 46, 47, 48

[56] References Cited

U.S. PATENT DOCUMENTS
4,375,965  3/1983  Weissman ................................. 433/37

FOREIGN PATENT DOCUMENTS
210868   11/1908  Germany ................................. 433/37
1079276   4/1960  Germany ................................. 433/45
3837585   5/1990  Germany ................................. 433/37

Primary Examiner—Cary E. O'Connor
Attorney, Agent, or Firm—J. Sanchelima

[57] ABSTRACT

A device for obtaining dental impressions to be used in the subsequent fabrication of a prosthesis. The dental impression device permits a more accurate impression by minimizing the interference typically encountered from the patient's segregation of saliva and/or the movement of his tongue. With a cooperating cover member that receives the U-shaped housing a dentist can force the moldable setting material conventionally used to conform to the area of the mouth being worked on. Openings selectively positioned on the upper wall of the housing member permit the injection of moldable material and other activities. A suction conduct is peripherally disposed around the lower edge of the U-shaped housing.

7 Claims, 3 Drawing Sheets

DENTAL IMPRESSION DEVICE

BACKGROUND OF THE INVENTION

1. Field of the Invention

The present invention relates to devices for obtaining dental impressions on patients, and more particularly, to those devices that involve the use of moldable substances that are forced to conform to the shape of the oral and dental structures being worked on for its accurate, prompt and reliable reproduction to be used in the fabrication of dental prosthesis, also to be able to isolate the tooth area from the cheek, tongue and any adjacent mucosa for the purpose of using rotary instrumentation for any type of cutting instrument in the area and not causing trauma or damage to any adjacent tissue.

2. Description of the Related Art

When a dentist takes an impression using conventional means available, a patient's saliva, inner walls of the oral cavity and tongue usually interfere with the procedure. There are a number of other dental procedures requiring the minimization of this interference, such as, fluoride, bleaching, bonding, tooth preparation, periodontal and other similar treatments. Many techniques have been used in the past to control these interfering factors, including the use of suction means, cotton and a quick efficient professional. However, the results have varied depending, among other things, on the cooperation of the patient, ability of the dentist and difficulty of the case.

SUMMARY OF THE INVENTION

It is one of the primary objects of the present invention to provide a dental impression device that minimizes the intrusion of saliva and interference by the patient's tongue with the impression process.

It is another object of the present invention to provide a device that pushes or packs the impression material with a positive force to make sure that the material reaches and adapts even to the smallest crevices.

It is another object of the present invention to provide a dental impression device that can be readily set up to force conventional moldable setting material around the area in the mouth being worked on with minimal interference from the patient's movements and secretion.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 2:
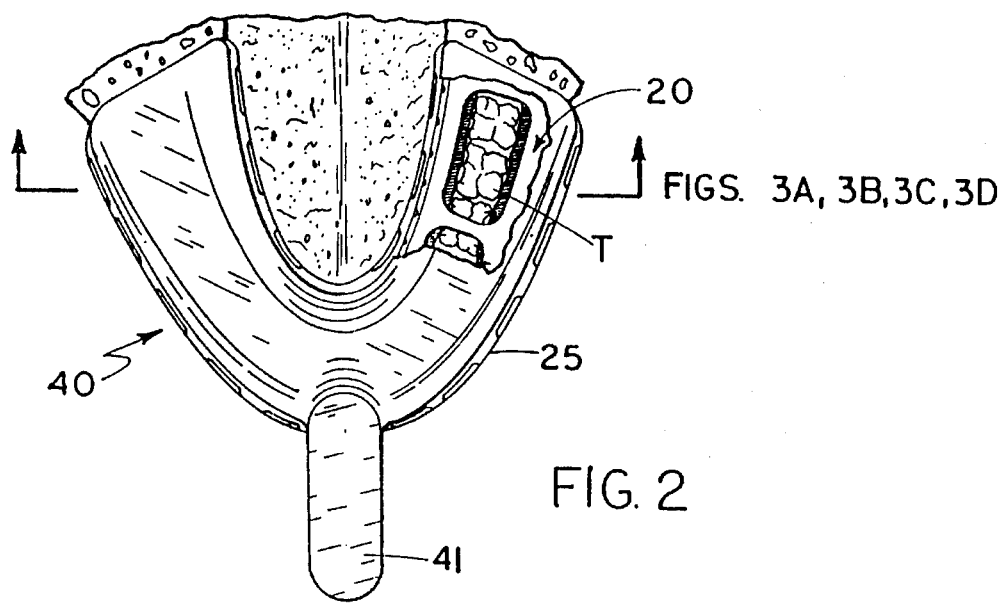
FIG. 2 shows a top view of the dental impression device with a partial cut on the cover assembly.
Figure 1:
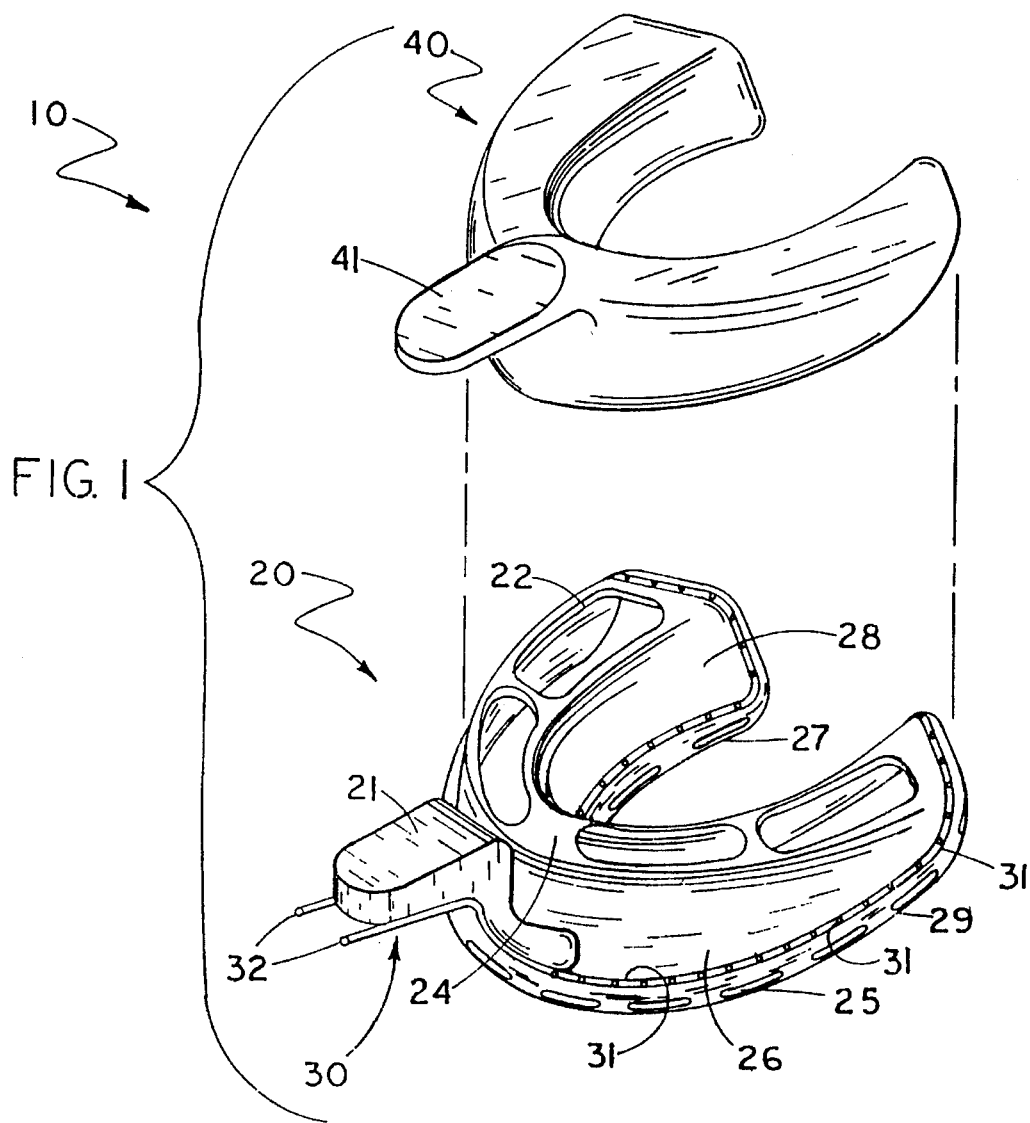
FIG. 1 represents an isometric view of the dental impression device comprising a main housing assembly and a cover assembly connected with projection lines.
Figure 3A:
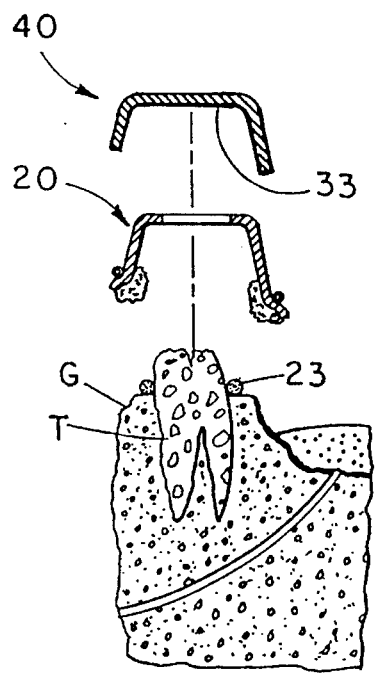
FIG. 3a is a cross-sectional elevational view of a tooth, main housing assembly and cover assembly in the initial step of use.
Figure 3B:
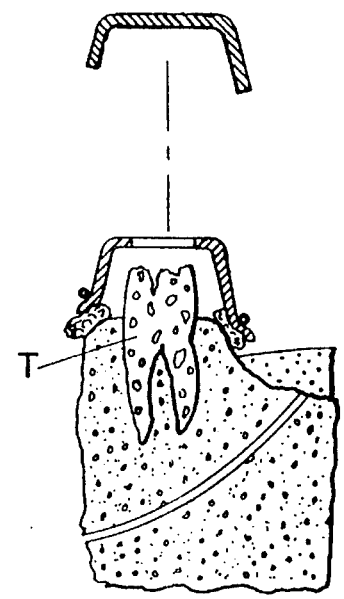
FIG. 3b shows a cross-sectional elevational view of the main housing assembly mounted over the gum with the putty seal in place, and the cover assembly above them.
Figure 3C:
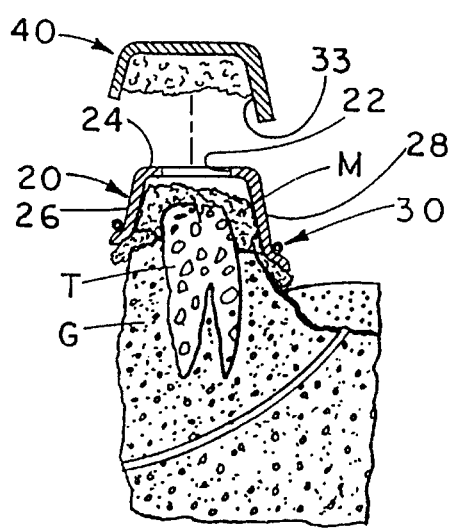
FIG. 3c shows a cross-sectional elevational view of the main housing in place and applying pressure to the impression material (putty) on the border with soft impression material inside, and the cover assembly also with soft impression material inside ready to be placed over the main housing assembly.
Figure 3D:
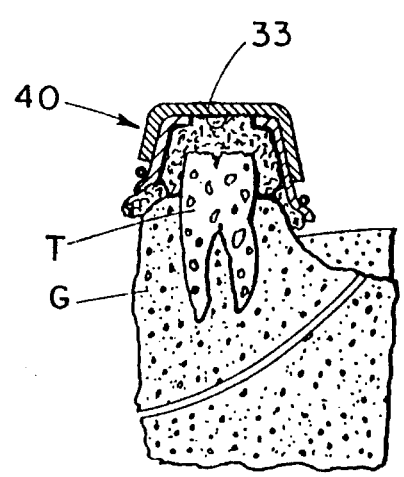
FIG. 3d is a cross-sectional elevational view of the cover assembly in place over the main housing applying pressure on the impression material.
Figure 4:
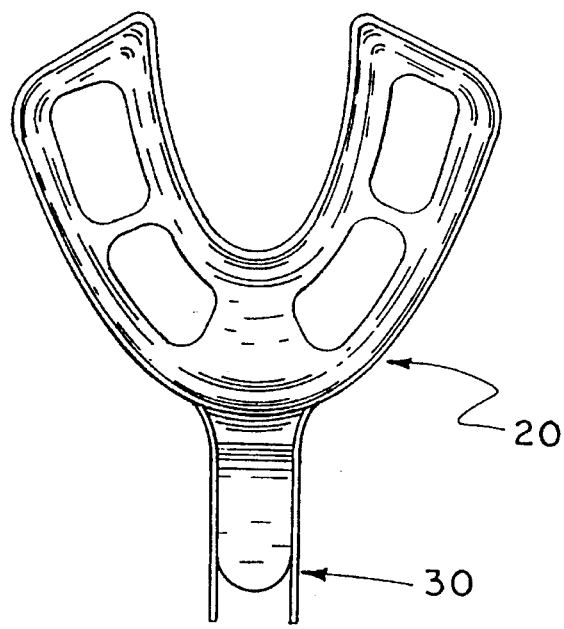
FIG. 4 is a bottom view of the main housing assembly.
Figure 5:
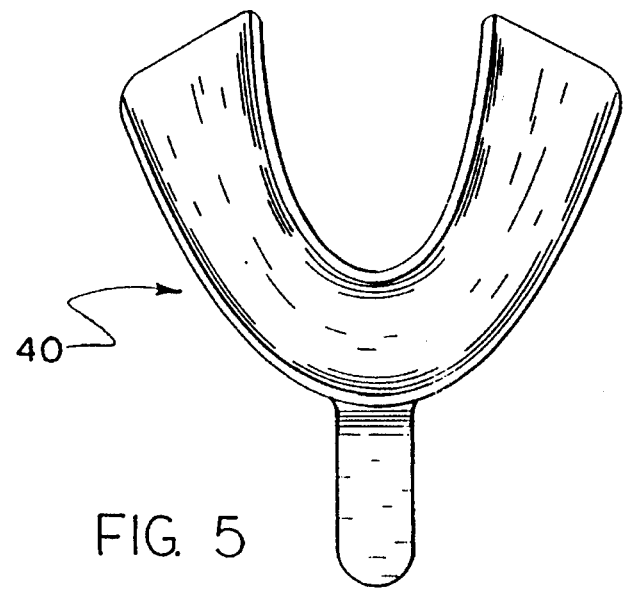
FIG. 5 is a bottom view of the cover assembly.
Figure 6:
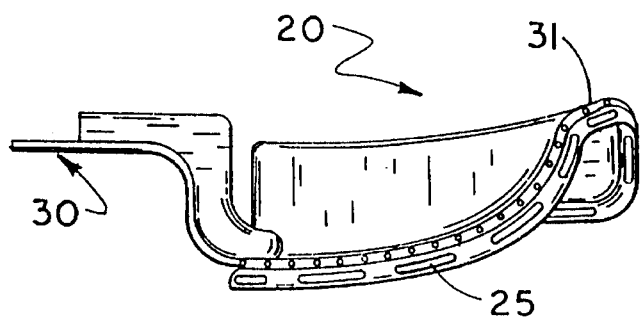
FIG. 6 is an elevational side view of the main housing assembly.

Referring now to the drawings, where the present invention is generally referred to with numeral 10, it can be observed that it basically includes main housing 20 and cover assembly 40 that cooperatively receives the former. Suction conduit assembly 30 is mounted along the periphery of the lower outer edge of main housing 20 which has substantially a U-shape to conform to a patient's jaw. Assembly 30 is intended to drain the saliva being constantly segregated. A plurality of openings 22 at upper wall 24 of housing 20 permit tooth T to be exposed when housing 20 is positioned over a user's jaw. As best seen in FIGS. 3a, 3b, 3c and 3d inner and outer lateral walls 26 and 28 extend peripherally down from upper wall 24. Lower edges 27 and 29 come in contact with the user's gum G. Openings 22 also permit the removal of the impression cord and the injection of impression material M when housing 20 is positioned over a user's jaw, as best seen in FIG. 3C.

Suction conduit assembly 30 is a continuous tube with perforations 31 for suctioning the saliva being constantly generated by the patient. Suction ports 32 are provided to connect conduit assembly 30 to a conventional low pressure resource or pump typically found in dental and medical environments. Two suction ports 32 are shown in the preferred embodiment since better cleansing and sterilization of suction assembly 30 can be achieved with an inlet and an outlet. Holes 25 are provided along the lower border of the main assembly for better retention of the putty material.

To use dental impression device 10, a dentist or his/her helper proceeds to prepare a user's mouth drying it up with cotton and suction means. As shown in FIGS. 3a through 3d, sealing putty is applied to the lower edges of main housing assembly 20 to prevent saliva from coming in. Main housing assembly 20 is made out of a rigid material, such as stainless steel or plastic, thereby preventing a patient's tongue from interfering. As shown in FIG. 3b, main housing assembly 20 is kept in place for a sufficient amount of time to permit the sealing putty to set up. After that, impression cord or rope 23 is removed to permit exposure of the tooth margin which lies at or within gingival sulcs. Then, as seen in FIG. 3c, soft impression material is injected inside the cavity defined by the interior of main housing assembly 20, tooth T and inside wall 33 the cover assembly 40. Finally, cover assembly 40 is placed over main housing assembly 20, pressing on the impression material M, until the material sets up and the tray with material is removed creating a negative mold or impression from which to construct a duplicate mold or cast of the original anatomical structure.

To facilitate the handling of housing assembly 20 and cover assembly 40, these assemblies are provided with handle members 21 and 41, respectively. In the preferred embodiment, suction ports 32 are positioned below handle member 21.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A device for obtaining a dental impression of a portion of a user's mouth with moldable setting material that is applied to the area being worked on including teeth, and said device comprising:

A. housing means having substantially a "U" shape that coincides with a user's gum and including an upper wall having a plurality of openings to permit injection of said moldable setting material therethrough when said housing means is positioned over said teeth, and said housing means further including inner and outer lateral walls that extend along the entire periphery of said housing means and ending with lower edges that come in contact with a user's gum to define a space therein;

B. cover means having substantially a "U" shape that cooperatively mounts over said housing means and is adapted to force said moldable setting material to conform to the shape of said area being worked on; and C. suction means mounted substantially close to said outer lower edge and extending along the outer periphery of said housing so that the saliva being segregated by said patient can be readily sucked in thereby minimizing its interference with the work being undertaken.

2. The devices set forth in claim 1 wherein said housing means includes a plurality of retention holes substantially adjacent to said lower edges.

3. The device set forth in claim 2 wherein said suction means includes conduit means with suction intake perforations that are peripherally disposed and substantially adjacent to said lower edges.

4. The device set forth in claim 3 wherein said housing means includes handle means rigidly mounted thereon to facilitate the mounting and removal of said housing means from a user's gum.

5. The device set forth in claim 4 wherein said cover means includes handle means rigidly mounted thereon to facilitate the mounting and removal of said cover means from a user's gum.

6. The device set forth in claim 1 wherein said housing means includes a plurality of retention holes substantially adjacent to said lower edges and handle means rigidly mounted thereon to facilitate the mounting and removal of said housing means from a user's gum.

7. The device set forth in claim 6 wherein said cover means includes handle means rigidly mounted thereon to facilitate the mounting and removal of said cover means from a user's gum.

* * * * *